United States Patent [19]

Wroblowsky et al.

[11] Patent Number: 4,636,245
[45] Date of Patent: Jan. 13, 1987

[54] HERBICIDAL TETRAHYDROTHIOPYRAN-2,4-DIONE DERIVATIVES, COMPOSITIONS, AND METHOD OF USE THEREFOR

[75] Inventors: Heinz-Jürgen Wroblowsky, Langenfeld; Jörg Stetter, Wuppertal; Ludwig Eue, Leverkusen; Robert R. Schmidt, Bergisch-Gladbach; Hans-Joachim Santel, Cologne, all of Fed. Rep. of Germany

[73] Assignee: Bayer Aktiengesellschaft, Leverkusen, Fed. Rep. of Germany

[21] Appl. No.: 737,292

[22] Filed: May 23, 1985

[30] Foreign Application Priority Data

Jun. 8, 1984 [DE] Fed. Rep. of Germany ....... 3421351

[51] Int. Cl.$^4$ .................. A01N 43/18; C07D 335/02; C07D 409/12
[52] U.S. Cl. ........................................... 71/90; 549/3; 549/28; 548/101; 548/136; 548/143; 548/186; 548/187; 548/214; 548/235; 548/247
[58] Field of Search .................... 71/90; 548/101, 136, 548/143, 186, 187, 214, 235, 247; 549/3, 28

[56] References Cited

U.S. PATENT DOCUMENTS 3,833,610 9/1974 Hardtmann ........................... 549/28

OTHER PUBLICATIONS

Iwataki et al., C.A., vol. 87, pp. 580–581, 87:84822b.
Iwataki et al., C.A., vol. 89, pp. 602–603, 89:43112t.
Sawaki et al., C.A., vol. 80, p. 411, 80:27103z.
Sawaki et al., C.A., vol. 82, p. 477, 82:170218n.

Primary Examiner—Henry R. Jiles
Assistant Examiner—J. G. Mullins
Attorney, Agent, or Firm—Sprung, Horn, Kramer & Woods

[57] ABSTRACT

Novel substituted tetrahydrothiopyran-2,4-dione herbicides of the formula

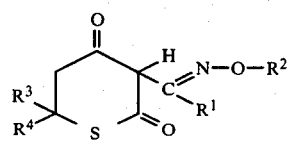

in which
$R^1$ is hydrogen, alkyl, alkenyl, alkinyl, alkoxyalkyl, alkylthioalkyl, halogenoalkyl, cycloalkyl or optionally substituted aryl,
$R^2$ is alkyl, alkenyl, alkinyl, alkoxyalkyl, alkylthioalkyl, halogenoalkyl, halogenoalkenyl, alkoxycarbonylalkyl, alkoximinoalkyl, optionally substituted aralkyl or optionally substituted heterocyclylalkyl, and
$R^3$ and $R^4$ each independently is hydrogen, alkyl, alkoxyalkyl, alkylthioalkyl, cycloalkyl, optionally substituted aryl, optionally substituted aryloxyalkyl or optionally substituted aralkyl,
or metal salts thereof.

11 Claims, No Drawings

HERBICIDAL TETRAHYDROTHIOPYRAN-2,4-DIONE DERIVATIVES, COMPOSITIONS, AND METHOD OF USE THEREFOR

The invention relates to new substituted tetrahydrothiopyran-2,4-diones, a process for their preparation, and their use as herbicides.

It is already known that certain α-pyrones, such as, for example, 3-(1-allyloximino-ethyl)-4-hydroxy-6-methyl-α-pyrone, possess herbicidal properties (see, for example, Japanese Patent No. 53/34,776 or DE-OS (German Published Specification) No. 2,317,987 or DE-AS (German Published Specification) No. 2,439,104).

However, the action of these compounds is not always completely satisfactory in all fields of use, particularly when low amounts and concentrations are used. New tetrahydrothiopyran-2,4-diones of the formula

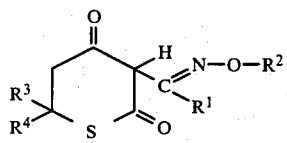

(I)

in which
$R^1$ represents hydrogen, alkyl, alkenyl, alkinyl, alkoxyalkyl, alkylthioalkyl, halogenoalkyl, cycloalkyl or optionally substituted aryl,
$R^2$ represents alkyl, alkenyl, alkinyl, alkoxyalkyl, alkylthioalkyl, halogenoalkyl, halogenoalkenyl, alkoxycarbonylalkyl, alkoximinoalkyl, optionally substituted aralkyl or optionally substituted heterocyclylalkyl and
$R^3$ and $R^4$ independently of one another each represent hydrogen, alkyl, alkoxyalkyl, alkylthioalkyl, cycloalkyl, optionally substituted aryl, optionally substituted aryloxyalkyl or optionally substituted aralkyl,
and their metal salts have been found.

The compounds according to the invention of the formula (I) occur in tautomeric equilibrium with compounds of the formulae (Ia), (Ib) and (Ic)

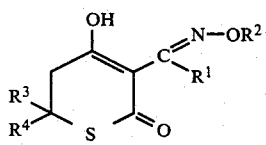

(Ia)

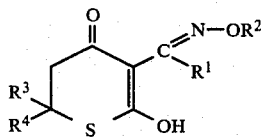

(Ib)

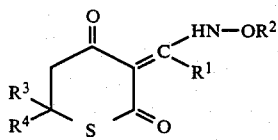

(Ic)

in which $R^1$, $R^2$, $R^3$ and $R^4$ have the meaning given above.

In particular, the enol forms (Ia) and (Ib) and the enamine structure (Ic) are stabilized by strong intramolecular hydrogen bridge bonds.

The compounds of the formula (I) can also occur as geometric and/or optical isomers or isomer mixtures of various compositions. Both the pure isomers and the isomer mixtures, as well as the various tautomeric structures, are claimed according to the invention.

It has furthermore been found that the new tetrahydrothiopyran-2,4-diones of the general formula (I) and their metal salts are obtained when aldehydes or ketones of the formula (II)

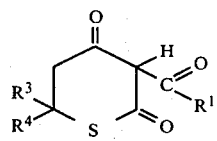

(II)

in which $R^1$, $R^3$ and $R^4$ have the meaning given above, are reacted with hydroxylamine derivatives of the formula (III)

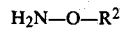

$H_2N\text{—}O\text{—}R^2$      (III)

in which $R^2$ has the meaning given above, or with their hydro salts, if appropriate in the presence of a diluent and, if appropriate, in the presence of an acid-binding agent, and, if required, the compounds of the formula (I) are converted to their metal salts in a manner which is in itself known.

Finally, it has been found that the new substituted tetrahydrothiopyran-2,4-diones of the formula (I) and their metal salts possess herbicidal properties, in particular selective herbicidal properties.

Surprisingly, the new substituted tetrahydrothiopyran-2,4-diones of the formula (I) and their metal salts exhibit a substantially better herbicidal activity than the α-pyrone derivatives, such as, for example, 3-(1-allyloximino-ethyl)-4-hydroxy-α-pyrone, which are known from the prior art and are similar compounds chemically and in terms of their action.

Formula (I) gives a general definition of the substituted tetrahydrothiopyran-2,4-diones according to the invention.

Preferred compounds of the formula (I) are those in which
$R^1$ represents hydrogen, alkyl, alkenyl, alkinyl, alkoxyalkyl, alkylthioalkyl or halogenoalkyl, each of which is straight-chain or branched and each of which has up to 8 carbon atoms in the individual alkyl or alkenyl or alkinyl parts and, where relevant, up to 9 identical or different halogen atoms, or represents cycloalkyl having 3 to 7 carbon atoms, or phenyl which is optionally monosubstituted or polysubstituted by identical or different substituents, suitable substituents being halogen, cyano, nitro and alkyl, alkoxy, alkylthio and halogenoalkyl, each of which is straight-chain or branched and each of which has up to 4 carbon atoms and, where relevant, up to 9 identical or different halogen atoms, $R^2$ represents alkyl, alkenyl, alkinyl, alkoxyalkyl, alkylthioalkyl, halogenoalkyl or halogenoalkenyl, each of which is straight-chain or branched and each of which has up to 8 carbon atoms in the individual alkyl or alkenyl or alkinyl parts and, where relevant, up to 9 identical or different halogen atoms, and furthermore represents alkoxycarbonylalkyl or alkoximinoalkyl, each of which is straight-chain or branched and each of which has up to 4 carbon atoms in the individual alkyl parts, or represents phenylalkyl which is optionally monosubstituted or polysubstituted by identical or different substituents and has up to 4 carbon atoms in the straight-chain or branched alkyl part, suitable phenyl substituents being those mentioned in the case of $R^1$, and furthermore represents a saturated or unsaturated 5-membered or 6-membered heterocyclic structure, each of which is bonded via an alkylene bridge having 1 to 4 carbon atoms, is optionally monosubstituted or polysubstituted by identical or different substituents from amongst halogen, lower alkyl and lower halogenoalkyl, and has 1 to 3 identical or different hetero atoms, suitable hetero atoms being: nitrogen, oxygen and sulphur, and $R^3$ and $R^4$ independently of one another represent hydrogen, or alkyl, alkoxyalkyl or alkylthioalkyl, each of which is straight-chain or branched and each of which has up to 8 carbon atoms in the individual alkyl parts, or represent cycloalkyl having 3 to 7 carbon atoms, or represent phenyl, phenylalkyl or phenoxyalkyl, each of which is optionally monosubstituted or polysubstituted by identical or different substituents and, where relevant, has 1 to 4 carbon atoms in the alkyl parts, suitable substituents being those mentioned in the case of $R^1$.

Particularly suitable compounds of the formula (I) are those in which $R^1$ represents hydrogen, methyl, ethyl, n- or i-propyl, n-, i-, s- or t-butyl, n- or i-pentyl, n- or i-hexyl, vinyl, allyl, n- or i-butenyl, n- or i-pentenyl, n- or i-hexenyl, propargyl, methylpropargyl, dimethylpropargyl, methoxymethyl, ethoxymethyl, isopropoxymethyl, methoxyethyl, ethoxyethyl, methylthiomethyl, methylthioethyl, ethylthioethyl, trifluoromethyl, dichlorofluoromethyl, difluorochloromethyl, trichloromethyl, dichloromethyl, chloromethyl, 2-chloroethyl, 2-bromoethyl, 2,2,2-trichloroethyl, 2,2,2-trifluoroethyl, cyclopropyl, cyclobutyl, cyclopentyl or cyclohexyl, or represents phenyl which is monosubstituted to trisubstituted by identical or different substituents from amongst fluorine, chlorine, bromine, cyano, nitro, methyl, methoxy or trifluoromethyl, $R^2$ represents methyl, ethyl, n- or i-propyl, n-, i-, s- or t-butyl, n- or i-pentyl, n- or i-hexyl, allyl, n- or i-butenyl, n- or i-pentenyl, propargyl, methoxymethyl, ethoxymethyl, isopropoxymethyl, methoxyethyl, ethoxyethyl, methylthiomethyl, methylthioethyl, ethylthioethyl, 2-chloroethyl, 2bromoethyl, 2,2,2-trifluoroethyl, 2,2,2-trichloroethyl, 3-chloropropenyl, methoxycarbonylmethyl, ethoxycarbonylmethyl, methoximinomethyl, methoximinoethyl or methoximinoprop-2-yl, or represents benzyl which is optionally monosubstituted to trisubstituted by identical or different substituents from amongst fluorine, chlorine, bromine, cyano, nitro, methyl, methoxy and trifluoromethyl, or represents a heterocyclic structure which is bonded via a methylene bridge, is optionally monosubstituted to trisubstituted by identical or different substituents from amongst chlorine, methyl and trifluoromethyl, and is of the formula

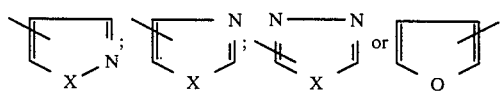

wherein X in each case represents oxygen or sulphur, and $R^3$ and $R^4$ independently of one another each represent hydrogen, methyl, ethyl, n- or i-propyl, n-, i-, s- or t-butyl, methoxymethyl, ethoxymethyl, methoxyethyl, ethoxyethyl, methylthiomethyl, ethylthiomethyl, ethylthioethyl, ethylthiopropyl, cyclopentyl or cyclohexyl, or represents phenyl, benzyl, phenylethyl, phenoxymethyl or phenoxyethyl, each of which is optionally monosubstituted to trisubstituted by identical or different substituents from amongst fluorine, chlorine, bromine, cyano, nitro, methyl, methoxy, ethoxy, methylthio, ethylthio and trifluoromethyl.

In addition to the compounds mentioned in the preparation examples, the following tetrahydrothiopyran-2,4 diones of the general formula (I) may be mentioned individually:

TABLE 1

| $R^1$ | $R^2$ | $R^3$ | $R^4$ |
|---|---|---|---|
| —CH₃ | —C₂H₅ | —CH₃ | —CH₃ |
| —CH₃ | —CH₂—CH=CH₂ | —CH₃ | —CH₃ |
| —CH₃ | —CH₂—CH=CH₂ | —H | —⟨phenyl⟩ |
| —C₂H₅ | —C₂H₅ | —CH₃ | —CH₃ |
| —C₂H₅ | —CH₂—CH=CH₂ | —CH₃ | —CH₃ |
| —C₂H₅ | —CH₂—CH=CH₂ | —CH₃ | —⟨phenyl⟩ |
| —C₃H₇ | —CH₃ | —CH₃ | —CH₃ |
| —C₃H₇ | —C₂H₅ | —CH₃ | —CH₃ |
| —C₃H₇ | —CH(CH₃)₂ | —CH₃ | —CH₃ |
| —C₃H₇ | —C₂H₅ | —H | —⟨phenyl⟩ |
| —C₃H₇ | —CH₂—CH=CH₂ | —CH₃ | —CH₃ |
| —C₃H₇ | —CH₂—CH=CH₂ | —H | —⟨2,4,6-trimethylphenyl⟩ |
| —C₃H₇ | —CH₂—C≡CH | —CH₃ | —CH₃ |
| —C₃H₇ | —CH₂—⟨5-methyl-isoxazol-3-yl⟩ | —CH₃ | —CH₃ |
| —C₃H₇ | —CH₂—⟨2-methyl-thiazol-4-yl⟩ | —CH₃ | —CH₃ |
| —C₃H₇ | —C₂H₅ | —H | —CH₂—CH(CH₃)(SC₂H₅) |

TABLE 1-continued

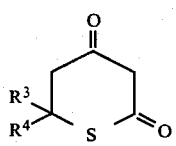
(I)

| $R^1$ | $R^2$ | $R^3$ | $R^4$ | |
|---|---|---|---|---|
| $-C_3H_7$ | $-C_2H_5$ | | $-H$ | −CH₂−CH(C₆H₅)(SC₂H₅) |
| $-C_3H_7$ | $-CH_2-CH=CH_2$ | | $-H$ | −CH₂−CH(CH₃)(SC₂H₅) |
| $-C_3H_7$ | $-CH_2-CH=CH_2$ | | $-H$ | −CH₂−CH(C₆H₅)(SC₂H₅) |
| $-C_3H_7$ | $-C_2H_5$ | | $-H$ | −C₆H₄−CH₃ |
| $-C_3H_7$ | $-C_2H_5$ | | $-H$ | −C₆H₄−Cl |
| $-C_3H_7$ | $-CH_2-CH=CH_2$ | | $-H$ | −C₆H₄−F |
| $-C_3H_7$ | $-CH(CH_3)-CH=N-OCH_3$ | $-CH_3$ | $-CH_3$ | |
| $-C_3H_7$ | $-CH_2-CH=N-OCH_3$ | $-CH_3$ | $-CH_3$ | |
| $-C_3H_7$ | $-CH(CH_3)-CH=N-OCH_3$ | | $-H$ | −C₆H₅ |
| $-C_3H_7$ | $-CH_2-CH=CH-Cl$ | $-CH_3$ | $-CH_3$ | |
| $-C_3H_7$ | $-C_2H_5$ | | $-H$ |  |
| $-C_3H_7$ | $-CH_2-CH=CH_2$ | | $-H$ | 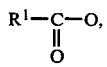 |
| $-C_3H_7$ | $-CH_2-O-CH_3$ | $-CH_3$ | $-CH_3$ | |
| $-C_3H_7$ | $-CH_2-S-CH_3$ | $-CH_3$ | $-CH_3$ | |
| $-C_3H_7$ | $-CH_2-C_6H_5$ | $-CH_3$ | $-CH_3$ | |

If, for example, 3-butyryl-6,6-dimethyl-tetrahydrothiopyran-2,4-dione and 0-allylhydroxylamine are used as starting materials, the course of the reaction of the process according to the invention can be represented by the following equation:

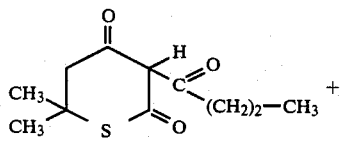 +

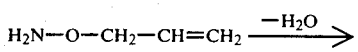

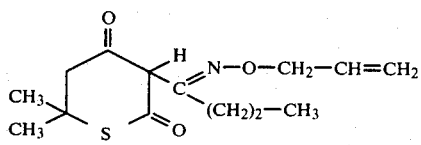

The formula (II) gives a general definition of the aldehydes or ketones required as starting materials for carrying out the process according to the invention. In this formula (II), $R^1$, $R^3$ and $R^4$ preferably represent those radicals which have already been mentioned in the description of the substances according to the invention, of the formula (I), as being preferred for these substituents.

The aldehydes and ketones of the formula (II) are unknown to date. They are obtained when tetrahydrothiopyran-2,4-diones of the formula (IV)

(IV)

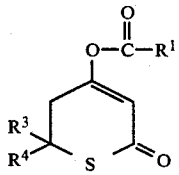

in which $R^3$ and $R^4$ have the meaning given above, are reacted with acylating agents of the formula (V)

$$R^1-\overset{O}{\underset{\|}{C}}-Y \qquad (V)$$

in which
$R^1$ has the meaning given above and
Y represents an electron-attracting leaving group, in particular halogen or the radical $$R^1-\overset{O}{\underset{\|}{C}}-O,$$

wherein $R^1$ has the meaning given above, the reaction either first being carried out in a first stage, if appropriate in the presence of a diluent (such as, for example, toluene) and, if appropriate, in the presence of an acid-binding agent (such as, for example, diazabicycloundecene (DBU)), at temperatures between $-20°$ C. and $+50°$ C., and the resulting 0-acyl derivatives of the formula (VI)

(VI)

in which $R^1$, $R^3$ and $R^4$ have the meaning given above, being subjected to a rearrangement reaction in a 2nd stage, if appropriate likewise in the presence of a diluent (such as, for example, toluene) and in the presence of a basic catalyst (such as, for example, 4-(N,N-dimethylamino)pyridine), at temperatures between 0° C. and +120° C., or being carried out in one reaction step, likewise in the presence of a diluent (such as, for example, pyridine) and, if appropriate, in the presence of a catalyst (such as, for example, zinc chloride), at temperatures between 0° C. and +150° C.

Some of the tetrahydrothiopyran-2,4-diones of the formula (IV) are known [see Monatshefte für Chemie 113, 1283–1297 (1982)].

The members which are unknown hitherto are obtained in a manner which is known in principle, for example when methyl vinyl ketones of the formula (VIII)

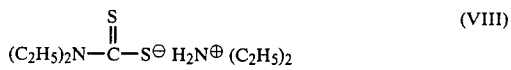

in which $R^3$ and $R^4$ have the meaning given above, are cyclied with diethylammonium N,N-diethyldithiocarbamate of the formula (VIII)

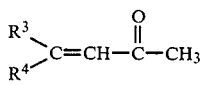

if appropriate in the presence of a diluent (such as, for example, bromobenzene), at temperatures between +50° C. and 200° C., and the resulting diethylamino compounds of the formula (IX)

in which $R^3$ and $R^4$ have the meaning given above, are first reacted with aqueous sodium hydroxide at temperatures between +30° C. and +150° C., and the resulting thiopyranthione compounds of the formula (X)

in which $R^3$ and $R^4$ have the meaning given above, are then reacted with aqueous hydrogen peroxide, if appropriate in the presence of a diluent (such as, for example, ethanol) and, if appropriate, in the presence of a basic catalyst (such as, for example, potassium hydroxide), at temperatures between −30° C. and +30° C.

The acylating agents of the formula (V), the methyl vinyl ketones of the formula (VII) and the diethylammonium N,N-diethyldithiocarbamate of the formula (VIII) are generally known compounds of organic chemistry.

Formula (III) gives a general definition of the hydroxylamine derivatives furthermore required as starting materials for carrying out the process according to the invention. In this formula (III), $R^2$ preferably represents those substituents which have already been mentioned in the description of the substances according to the invention, of the formula (I), as being preferred for these radicals.

The hydroxylamine derivatives of the formula (III) and their hydro salts are likewise generally known compounds of organic chemistry.

Suitable diluents for carrying out the process according to the invention are inert organic solvents. Alcohols or aqueous alcohol mixtures, for example methanol, ethanol, n- and i-propanol and their mixtures with water, are preferably used.

If the hydroxylamine derivatives of the formula (III) are employed in the form of their salts—hydrochlorides are preferably used—the reaction is usually carried out in the presence of an acid-binding agent.

Suitable acid-binding agents are all customary inorganic or organic bases. These include, for example, alkali metal hydroxides, such as sodium hydroxide or potassium hydroxide, alkali metal carbonates, such as sodium carbonate, potassium carbonate or sodium bicarbonate, alkali metal acetates, such as sodium acetate, and alkali metal alcoholates, such as sodium methylate, potassium methylate, sodium ethylate or potassium ethylate.

In carrying out the process according to the invention, the reaction temperatures can be varied within a relatively wide range. In general, the reaction is carried out at between 0° C. and +150° C., preferably between 20° C. and +100° C.

In carrying out the process according to the invention, in general 1.0 to 2.0 mols, preferably 1.0 to 1.5 mols, of the hydroxylamine derivative of the formula (III) and, if appropriate, 1.0 to 2.0 mols, preferably 1.0 to 1.5 mols, of the acid-binding agent are employed per mol of the aldehyde or ketone of the formula (II). Working up and isolation of the reaction products of the formula (I) are carried out by customary methods.

For the preparation of metal salts of the compounds of the formula (I), preferred salts are those of metals of main groups I to IV and of sub-groups I and II and IV to VIII, and sodium, potassium, copper, zinc, manganese, magnesium, calcium, barium, tin, iron, cobalt and nickel may be mentioned as examples.

To prepare the sodium and potassium salts, a compound of the formula (I), in aqueous solution or in an organic solvent, such as acetone, methanol, ethanol or dimethylformamide, is reacted with sodium hydroxide or potassium hydroxide, and the salts are isolated by filtering them off or by evaporating down the solution, and, if required, are purified by recrystallization.

The calcium, barium, magnesium, manganese, copper, nickel, tin, iron and cobalt salts are prepared from the sodium salts by treatment with an appropriate inorganic metal salt, for example calcium chloride, barium chloride, copper sulphate, nickel chloride or cobalt nitrate. The calcium salts can also be prepared by treating a compound of the formula (I) with calcium hydroxide.

The active compounds according to the invention can be used as defoliants, desiccants, agents for destroying broad-leaved plants and, especially, as weedkillers. By weeds, in the broadest sense, there are to be understood plants which grow in locations where they are undesired. Whether the substances according to the invention act as total or selective herbicides depends essentially on the amount used.

The compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds according to the invention can be employed with particularly good success for combating monocotyledon weeds in dicotyledon cultures, such as, for example, in sugar beet, soy beans or cotton.

The compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The compounds according to the invention, as such or in the form of their formulations, can also be used, for combating weeds, as mixtures with known herbicides, finished formulations or tank mixtures being possible.

Possible components for the mixtures are known herbicides, such as, for example, 1-amino-6-ethylthio-3-(2,2-dimethylpropyl)-1,3,5-triazine-2,4(1H,3H)-dione or N-2-(benzothiazolyl)-N,N'-dimethylurea for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one or known nitrodiphenyl ethers for combating weeds in soy beans, and known ureas in cotton or field beans. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

Preparation Examples

EXAMPLE 1

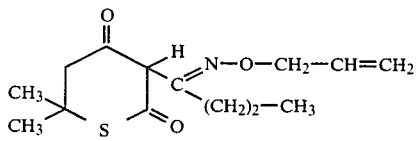

4.2 g (0.07 mol) of sodium methylate are added to 8.5 g (0.077 mol) of 0-allylhydroxylamine hydrochloride in 50 ml of methanol, while stirring and cooling with ice, and the mixture is stirred for a further 15 minutes at room temperature. The mixture is filtered, and the filtrate is added to a solution of 16 g (0.07 mol) of 6,6-dimethyl-3-butyryltetrahydrothiopyran-2,4-dione. The reaction mixture is stirred at room temperature until the conversion is complete (monitored by means of thin-layer chromatography/chloroform+2% of methanol/-silica gel) and is evaporated down in vacuo, the residue is taken up in water, the solution is extracted with chloroform, the combined organic phases are washed with 5% strength hydrochloric acid, dried over sodium sulphate and freed from the solvent in vacuo. 15.8 g (80% of theory) of 3-(1-allyloximino-butyl)-6,6-dimethyl-tetrahydrothiopyran-2,4dione are obtained as a red oil of refractive index $n_D^{22.8}$: 1.5358.

Preparation of the starting compound:

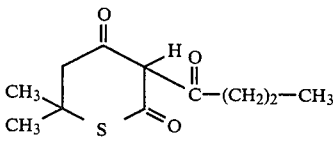

27.1 g (0.12 mol) of 6,6-dimethyl-4-butyryloxy-5,6-dihydro-α-thiopyrone and 0.01 g (0.1 mmol) of 4-(N,N-dimethylamino)-pyridine in 150 ml of toluene are heated at the boil (approx. 3 hours) until analysis by thin-layer chromatography (silica gel/dichloromethane or chloroform+2% of methanol) indicates that conversion of the starting material is complete (on treatment with aqueous Fe(III) chloride solution, the product gives an intense orange-red coloration). To work up the mixture, it is washed with dilute hydrochloric acid and dried over magnesium sulphate, and the solvent is removed in vacuo. 15.1 g (55% of theory) of 6,6-dimethyl-3-butyryltetrahydrothiopyran-2,4-dione are obtained as an oil.

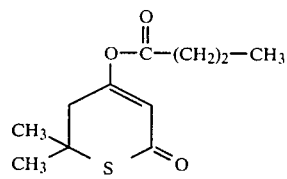

13.9 g (0.13 mol) of butyryl chloride are added dropwise, at 0° C. and while stirring, to 20 g (0.12 mol) of 6,6-dimethyltetrahydrothiopyran-2,4-dione and 19.9 g (0.13 mol) of diazabicycloundecene (DBU) in 240 ml of toluene and, when the addition is complete, stirring is continued for a further 2 hours at 0° C. and 120 ml of water are added. The organic phase is separated off, the aqueous phase is extracted twice with toluene, and the combined organic phases are washed with 5% strength hydrochloric acid and with saturated aqueous sodium chloride solution, dried over magnesium sulphate and freed from the solvent in vacuo. 27.1 g (93.5% of theory) of 6,6-dimethyl-4-butyryloxy-5,6-dihydro-α-thiopyrone are obtained as an oil, which can be employed in the next stage without further purification.

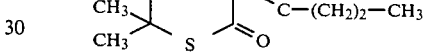

(alternative preparation)

9.6 g (0.07 mol) of zinc chloride are first added to 5 g (0.035 mol) of 6,6-dimethyltetrahydrothiopyran-2,4-dione in 100 ml of pyridine, after which 3.7 g (0.03 mol) of butyryl chloride are added dropwise. When the addition is complete, the mixture is heated to the reflux temperature for 4 hours, and the cooled reaction mixture is poured into 200 ml of semi-concentrated hydrochloric acid, the mixture is extracted several times with dichloromethane, the combined organic phases are dried over magnesium sulphate, and the solvent is removed in vacuo. 2.9 g (36.6% of theory) of 6,6-dimethyl-3-butyryltetrahydrothiopyran-2,4-dione are obtained as an oil.

The following tetrahydrothiopyran-2,4-diones of the general formula (I) are obtained in a corresponding manner and in accordance with the general preparation data:

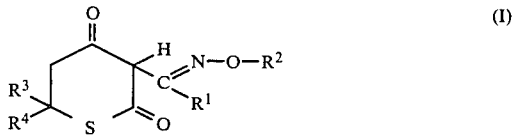

TABLE 2

| Example No. | $R^1$ | $R^2$ | $R^3$ | $R^4$ | Refractive index/melting point |
|---|---|---|---|---|---|
| 2 | $CH_3-(CH_2)_2-$ | $C_2H_5-$ | $CH_3-$ | $CH_3-$ | $n_D^{23.6}$:1.5390 |
| 3 | $CH_3-(CH_2)_2-$ | $(CH_3)_2CH-$ | $CH_3-$ | $CH_3-$ | $n_D^{22.8}$:1.5317 |

TABLE 2-continued

| Example No. | R¹ | R² | R³ | R⁴ | Refractive index/melting point |
|---|---|---|---|---|---|
| 4 | phenyl | $C_2H_5-$ | $CH_3-$ | $CH_3-$ | mp:78°–81° C. |
| 5 | phenyl | $CH_2=CH-CH_2-$ | $CH_3-$ | $CH_3-$ | mp:119–122° C. |
| 6 | $CH_3-(CH_2)_2-$ | $CH_2-CH=CHCl$ | $CH_3-$ | $CH_3-$ | $n_D^{22}:1.5509$ |

USE EXAMPLES

In the use examples below, the compound shown below was used as a comparative example:

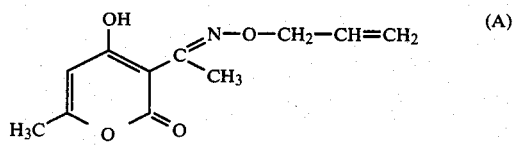

3-(1-allyloximino-ethyl)-4-hydroxy-6-methyl-α-pyrone (see, for example, DE-AS (Germans Published Specification) No. 2,439,104).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0% = no action (like untreated control)
100% = total destruction.

In this test, a clearly superior activity compared with the prior art is shown, for example, by the compound according to preparation Example 1.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% = no action (like untreated control)
100% = total destruction.

In this test, a clearly superior activity compared with the prior art is shown, for example, by the compound according to preparation Example 1.

It will be understood that the specification and examples are illustrative but not limitative of the present invention and that other embodiments within the spirit and scope of the invention will suggest themselves to those skilled in the art.

What is claimed is:

1. A substituted tetrahydrothiopyran-2,4-dione of the formula

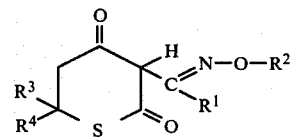

in which
R¹ is hydrogen, alkyl, alkenyl, alkinyl, alkoxyalkyl, alkylthioalkyl or halogenoalkyl, each of which has up to 8 carbon atoms in the individual alkyl or alkenyl or alkinyl parts and, where relevant, up to 9 identical or different halogen atoms, or is cycloalkyl having 3 to 7 carbon atoms, phenyl, or phenyl substituted by halogen, cyano, nitro and alkyl, alkoxy, alkylthio and/or halogenoalkyl, each of which has up to 4 carbon atoms and, where relevant, up to 9 identical or different halogen atoms,
R² is alkyl, alkenyl, alkinyl, alkoxyalkyl, alkylthioalkyl, halogenoalkyl or halogenoalkenyl, each of which has up to 8 carbon atoms in the individual alkyl or alkenyl or alkinyl parts and, where relevant, up to 9 identical or different halogen atoms, or is alkoxycarbonylalkyl or alkoximinoalkyl, each of which has up to 4 carbon atoms in the individual alkyl parts, or is phenylalkyl which has up to 4 carbon atoms in the straight-chain or branched alkyl part and is unsubstituted or substituted in the phenyl part by those substituents mentioned in the case of $R^1$, or is

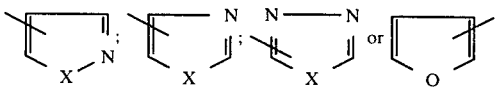

wherein X is oxygen or sulphur, each of which is bonded via an alkylene bridge having 1 to 4 carbon atoms and is unsubstituted or substituted by halogen, lower alkyl and/or lower halogenoalkyl, and $R^3$ and $R^4$ each independently is hydrogen, or alkyl, alkoxyalkyl or alkylthioalkyl, each of which has up to 8 carbon atoms in the individual alkyl parts, or is cycloalkyl having 3 to 7 carbon atoms, or is phenyl, phenylalkyl or phenoxyalkyl, each of which is unsubstituted or substituted by those substituents mentioned in the case of $R^1$ and, where relevant, has 1 to 4 carbon atoms in the alkyl part, or a metal salt thereof.

2. A compound or salt according to claim 1, in which
$R^1$ is hydrogen, methyl, ethyl, n- or i-propyl, n-,i-, s- or t-butyl, n- or i-pentyl, n- or i-hexyl, vinyl, allyl, n- or i-butenyl, n- or i-pentenyl, n- or i-hexenyl, propargyl, methylpropargyl, dimethylpropargyl, methoxymethyl, ethoxymethyl, isopropoxymethyl, methoxyethyl, ethoxyethyl, methylthiomethyl, methylthioethyl, ethylthioethyl, trifluoromethyl, dichlorofluoromethyl, difluorochloromethyl, trichloromethyl, dichloromethyl, chloromethyl, 2-chloroethyl, 2-bromoethyl, 2,2,2-trichloroethyl, 2,2,2-trifluoroethyl, cyclopropyl, cyclobutyl, cyclopentyl or cyclohexyl, or is phenyl which is monosubstituted trisubstituted by fluorine, chlorine, bromine, cyano, nitro, methyl, methoxy and/or trifluoromethyl, $R^2$ is methyl, ethyl, n- or i-propyl, n-, i-, s- or t-butyl, n- or i-pentyl, n- or i-hexyl, allyl, n- or i-butenyl, n- or i-pentenyl, propargyl, methoxymethyl, ethoxymethyl, isopropoxymethyl, methoxyethyl, ethoxyethyl, methylthiomethyl, methylthioethyl, ethylthioethyl, 2-chloroethyl, 2-bromoethyl, 2,2,2-trifluoroethyl, 2,2,2-trichloroethyl, 3-chloropropenyl, methoxycarbonylmethyl, ethoxycarbonylmethyl, methoximinomethyl, methoximinoethyl or methoximinoprop-2-yl, or is benzyl which is unsubstituted or monosubstituted to trisubstituted by fluorine, chlorine, bromine, cyano, nitro, methyl, methoxy and/or trifluoromethyl, or is a heterocyclic structure which is bonded via a methylene bridge and which is unsubstituted or monosubstituted to trisubstituted by chlorine, methyl and/or trifluoromethyl, and is of the formula

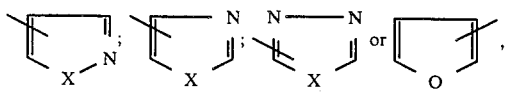

X is oxygen or sulphur, and
$R^3$ and $R^4$ each independently is hydrogen, methyl ethyl, n- or i-propyl, n-, i-, s- or t-butyl, methoxymethyl, ethoxymethyl, methoxyethyl, ethoxyethyl, methylthiomethyl, ethylthiomethyl, ethylthioethyl, ethylthiopropyl, cyclopentyl or cyclohexyl, or is phenyl, benzyl, phenylethyl, phenoxymethyl or phenoxyethyl, each of which is optionally monosubstituted to trisubstituted by fluorine, chlorine, bromine, cyano, nitro, methyl, methoxy, ethoxy, methylthio, ethylthio and/or trifluoromethyl.

3. A compound of the formula

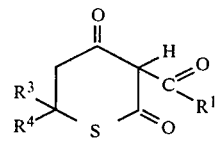

in which
$R^1$ is hydrogen, alkyl, alkenyl, alkinyl, alkoxyalkyl, alkylthioalkyl or halogenoalkyl, each of which has up to 8 carbon atoms in the individual alkyl or alkenyl or alkinyl parts and, where relevant, up to 9 identical or different halogen atoms, or is cycloalkyl having 3 to 7 carbon atoms, or phenyl which is unsubstituted on substituted by halogen, cyano, nitro and alkyl, alkoxy, alkylthio and/or halogenoalkyl, each of which has up to 4 carbon atoms and, where relevant, up to 9 identical or different halogen atoms, and $R^3$ and $R^4$ each independently is hydrogen, or alkyl, alkoxyalkyl or alkylthioalkyl, each of which has up to 8 carbon atoms in the individual alkyl parts, or is cycloalkyl having 3 to 7 carbon atoms, or is phenyl, phenylalkyl or phenoxyalkyl, each of which is unsubstituted or substituted by those substituents mentioned in the case of $R^1$ and, where relevant, has 1 to 4 carbon atoms in the alkyl part, or a metal salt thereof.

4. A compound according to claim 1, wherein such compound is 3-(1-allyloximino-butyl)-6,6,-dimethyl-tetrahydrothiopyran-2,4-dione of the formula

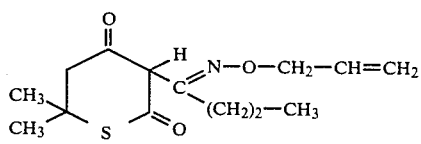

or a metal salt thereof.

5. A compound according to claim 1, wherein such compound is 6,6-dimethyl-3-(1-ethoximino-butyl)-tetrahydrothiopyran-2,4-dione of the formula

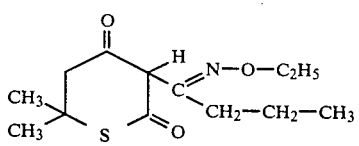

or a metal salt thereof.

6. A compound according to claim 1, wherein such compound is 6,6-dimethyl-3-(1-isopropoximino-butyl)-tetrahydrothiopyran-2,4-dione of the formula

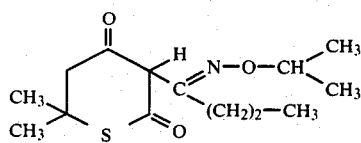

or a metal salt thereof.

7. A compound according to claim 1, wherein such compound is 6,6-dimethyl-3-(α-ethoximino-benzyl)-tetrahydrothiopyran-2,4-dione of the formula

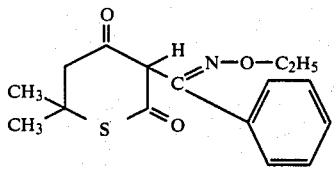

or a metal salt thereof.

8. A compound according to claim 1, wherein such compound is 3-(α-allyloximino-benzyl)-6,6-dimethyl-tetrahydrothiopyran-2,4-dione of the formula

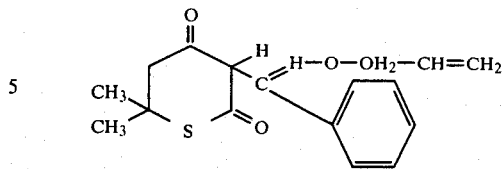

or a metal salt thereof.

9. A herbicidal composition comprising a herbicidally effective amount of a compound or salt according to claim 1 in admixture with a diluent.

10. A method of combating unwanted vegetation which comprises applying to such vegetation or to a locus from which it is desired to exclude such vegetation a herbicidally effective amount of a compound or salt according to claim 1.

11. The method according to claim 10, wherein such compound is
3-(1-allyloximino-butyl)-6,6-dimethyl-tetrahydrothiopyran-2,4-dione
6,6-dimethyl-3-(1-ethoximino-butyl)-tetrahydrothiopyran-2,4-dione
6,6-dimethyl-3-(1-isopropoximino-butyl)-tetrahydrothiopyran-2,4-dione
6,6-dimethyl-3-(α-ethoximino-benzyl)-tetrahydrothiopyran-2,4-dione or
3(α-allyloximino-benzyl)-6,6-dimethyl-tetrahydrothiopyran-2,4-dione,
or a metal salt thereof.

* * * * *

UNITED STATES PATENT AND TRADEMARK OFFICE
CERTIFICATE OF CORRECTION

PATENT NO. : 4,636,245

DATED : January 13, 1987

INVENTOR(S) : Heinz-Jürgen Wroblowsky, et al.

It is certified that error appears in the above-identified patent and that said Letters Patent is hereby corrected as shown below:

| | |
|---|---|
| Col. 3, line 50 | Before "bromoethyl" insert -- - -- |
| Col. 11, line 33 | After "4" insert -- - -- |
| Col. 6, line 68 | After "-dimethylamino)" insert -- - -- |
| Col. 13, line 29 | Before "published" delete "Germans" and substitute --German-- |
| Col. 15, line 37 | Before "trisubstituted" insert --to-- |
| Col. 16, lines 1 and 2 | Before "monosubstituted" delete "optionally" and substitute --unsubstituted or-- |
| Col. 16, line 24 | Before "substituted" delete "on" and substitute --or-- |
| Col. 18, line 3 | End of formula delete "H-O-OH$_3$-" and substitute --N-O-CH$_3$-- |

Signed and Sealed this

Twenty-fourth Day of May, 1988

Attest:

DONALD J. QUIGG

Attesting Officer

Commissioner of Patents and Trademarks